US005336795A

United States Patent [19]

Lisowsky

[11] Patent Number: 5,336,795

[45] Date of Patent: Aug. 9, 1994

[54] PROCESS FOR THE PREPARATION OF TRANSITION METAL COMPLEXES HAVING MONOSUBSTITUTED CYCLOPENTADIENYL LIGANDS

[75] Inventor: Richard Lisowsky, Kamen, Fed. Rep. of Germany

[73] Assignee: Witco GmbH, Bergkamen, Fed. Rep. of Germany

[21] Appl. No.: 196,638

[22] Filed: Feb. 15, 1994

[30] Foreign Application Priority Data

Apr. 15, 1993 [DE] Fed. Rep. of Germany ....... 4312270

[51] Int. Cl.[5] ........................ C07F 17/00; C07F 17/02; C07F 15/00; C07F 7/28

[52] U.S. Cl. ........................................ 556/56; 556/43; 556/53; 556/58; 556/63; 556/144; 556/1; 534/15

[58] Field of Search ........................ 556/43, 53, 56, 58, 556/63, 144, 1; 534/15

[56] References Cited

PUBLICATIONS (Houben-Weyl-Band 5/1c-Methoden der Organischen Chemie, Eugen Müller Verlag (Herausgeber)-Vierte Auflage (1970)-S. 660-667; George Thieme Verlag, Stuttgart.

Metallocene: Gmelin Handbuch der anorganischen Chemie-Ergänzungswerk zur 8. Auflage-Band 10 und 11: "Zirkonium-und Hafnium-Organische Verbindungen" S. 26 ff-Verlag Chemie, Weinheim (1973).

D. J. Cardin et al., *Chemistry of Organo-Zirconium and-Hafnium Compounds*, Chapter 1, pp. 11-31; Chapter 5, pp. 76-123; Chapter 20, pp. 399-439 (1986).

Izv. Vyssh. Uchebn, Zaved, Khim, Khim, Tekhnol., 26(6), 759-761 (1983); Chemical Abstract: 99: 157869 g.

Vestsi Akad. Navuk. BSSr, Ser. Khim Navuk., 1988(1), S. 96-97; Chemical Abstract: (109) 148913 q.

*Primary Examiner*—José G. Dees
*Assistant Examiner*—Porfirio Nazario-Gonzalez
*Attorney, Agent, or Firm*—Scully, Scott, Murphy & Presser

[57] ABSTRACT

Disclosed is a process for the preparation of transition metal complexes having monosubstituted cyclopentadienyl ligands of the general formula:

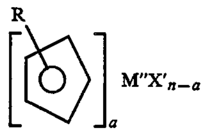

in which monomeric cyclopentadiene is reacted with organic halides or pseudohalides, using a mixture of an alkali metal oxide or hydroxide and an alkaline earth metal oxide or hydroxide as metallating agent in glycol diether as solvent, to form the intermediate monosubstituted cyclopentadiene, which in situ is metallated and reacted with a transition metal halide to give the final product.

5 Claims, No Drawings

PROCESS FOR THE PREPARATION OF TRANSITION METAL COMPLEXES HAVING MONOSUBSTITUTED CYCLOPENTADIENYL LIGANDS

BACKGROUND OF THE INVENTION

The invention relates to a process which, starting from cyclopentadiene (Cp), allows the preparation of transition metal complexes bearing monosubstituted cyclopentadienyl ligands in high yields without isolation of the intermediate stages, even on an industrial scale.

Due to the great variety of possible applications of the above mentioned transition metal complexes as catalysts in organic synthesis and, in particular, in the polymerization of olefins, the ability to efficiently prepare, in industry, sandwich complexes which are monosubstituted on the cyclopentadienyl radicals has become increasingly important.

The synthesis of such compounds is known in principle. It proceeds according to the reaction equations I and II:

$$\text{I). } Cp \xrightarrow[\text{2.) R-halide}]{\text{1.) M}} CpR$$

$$\text{II.) } 2\,CpR \xrightarrow[-2\,MX]{\text{1.) 2 M; 2.) } M'X_n} RCp_2M'X_{n-2}$$

with: M=metallating agent (e.g. Na, K, alkyllithium)
M'=transition metal (e.g. Fe, Ti, Zr, Hf)
X=Cl, Br, I
R=alkyl, cycloalkyl, benzyl, vinyl, allyl
n=2-4

A disadvantage here is that the substituted cyclopentadiene (CpR) must be prepared separately, before it can be reacted further.

The yields of CpR in stage I are often only small, so that complicated removal of byproducts is needed before appropriately pure product can be obtained for a further reaction.

The ability of the monoalkylcyclopentadienyl compounds to form dimers by an intermolecular Diels-Alder reaction complicates the purification, since the monomer can only be obtained in pure form by multiple distillation and thermal retro-Diels-Alder reaction. However, only these monomers can be used for the reaction according to equation II. Due to the above mentioned tendency to dimer formation, they are not stable in storage and before use again require the effort of thermal dimer removal. (Houben-Weyl Volumen 5/1c—Methoden der Organischen Chemie, editor Eugen Müller—fourth edition (1970)—pp. 660-667; Georg Thieme Verlag, Stuttgart;—Metallocenes: Gmelin Handbuch der anorganischen Chemie—supplement to 8th edition—Volumes 10 and 11: "Zirkonium-und Hafnium-Organische Verbindungen" [Organozirconium and organohafnium compounds] p. 26 ff—Verlag Chemie, Weinheim—1973; "Chemistry of Organo-Zirconium and Hafnium Compounds", D. J. Cardin; M. F. Lappert; C. L. Raston; 1986, Ellis Horwood Limited).

Although the yields of monosubstituted cyclopentadiene derivatives according to equation I could be improved in individual cases, the compounds are obtained either in a form which is still not pure enough for the reaction according to equation II or in a solvent which is unsuitable for a reaction according to equation II and must therefore be removed beforehand, which leads to losses in yield and the above-mentioned problems of dimerization (Izv. Vyssh. Uchebn, Zaved., Khim, Khim, Tekhnol., 26(6), 759-761; CA:99:157869 g).

There is therefore particular commercial and technical interest in a process which avoids the stated disadvantages and makes possible the preparation of metallocenes which are monosubstituted on the cyclopentadiene rings in a simple reaction procedure with improved yields even on a commercial scale.

BRIEF SUMMARY OF THE INVENTION

Surprisingly, it has now been found that the above-mentioned reactions of cyclopentadiene with organic halides give high yields and high purities (≧95%) of correspondingly monosubstituted cyclopentadienes which can be further converted, without isolation and without dimerization, directly into corresponding metallocenes in high yields and high purity.

The invention therefore provides a process for the preparation of transition metal complexes having monosubstituted cyclopentadienyl ligands of the general formula:

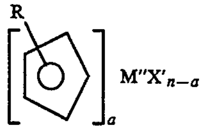

where

R is a $C_1$-$C_{30}$-alkyl group, $C_2$-$C_{30}$-alkenyl group, $C_7$-$C_{30}$-alkylaryl group, $C_8$-$C_{30}$-alkenylaryl group, $C_3$-$C_{12}$-alkoxyalkyl group, $C_1$-$C_{30}$-fluoroalkyl group or an organo-element radical such as $C_1$-$C_6$-alkyl-tri($C_1$-$C_{10}$-alkyl)silyl M" is a transition metal (Ti, Zr, Hf, Fe, V, Cr, Sc)

X' is Cl, Br, I n is the oxidation number of the transition metal a is at least 1 and a is≦n.

The process is characterized in that monomeric cyclopentadiene is reacted with organic halides or pseudohalides, using a mixture of an alkali metal oxide or hydroxide and an alkaline earth metal oxide or hydroxide as metallating agent in glycol diether as solvent, to form the intermediate monosubstituted cyclopentadiene, which in situ is metallated and reacted with a transition metal halide to given the final product.

Preferred substituents R are $C_3$-$C_{18}$-alkyl groups, $C_2$-$C_{18}$-alkenyl groups, $C_3$-$C_6$-alkoxyalkyl groups, $C_1$-$C_3$-alkyl-tri ($C_1$-$C_6$-alkyl)-silyl groups, in particular $C_3$-$C_8$-alkyl groups, $C_2$-$C_6$-alkenyl groups.

The transition metal used is, preferably, titanium, zirconium or hafnium.

The invention furthermore relates to the new compound bis(octadecylcyclopentadienyl)$ZrCl_2$.

The process is explained below with the aid of the following reaction scheme:

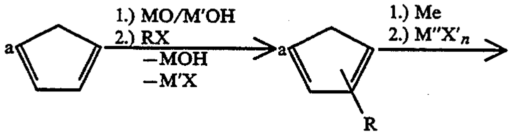

-continued

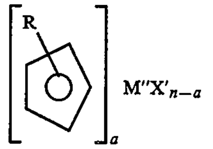

where:

M is an alkali or alkaline earth metal

M' is an alkali or alkaline earth metal (provided that an alkali and an alkaline earth metal are both present)

is a $C_1$–$C_{30}$-alkyl group, $C_2$–$C_{30}$-alkenyl group, $C_7$–$C_{30}$-alkylaryl group, $C_8$–$C_{30}$-alkenylaryl group, $C_3$–$C_{12}$-alkoxyalkyl group, $C_1$–$C_{30}$-fluoroalkyl group or an organo-element radical such as $C_1$–$C_6$-alkyl-tri($C_1$–$C_{10}$-alkyl)silyl X is halogen such as Cl, Br or I, or $—OSO_2R'$ (R':alkyl, p-tolyl)

Me is a metallating agent (Li, Na, K, NaH, KH, alkyllithiums, etc. (agents known from the literature for metallating monomeric cyclopentadienes)

M'' is a transition metal, such as Fe, V, Cr or Sc or in particular Ti, Zr or Hf, or a mixture of such transition metals X' is Cl, Br or I, or a mixture thereof n is the oxidation number of the transition metal a is at least 1 and is $\leq$n, and a is the number of the groups X' which are to be substituted on the transition metal.

The mixture of a metal oxide and a metal hydroxide is suspended in glycol diether. In principle, all combinations of alkali and alkaline earth metal oxides and hydroxides can be considered here.

Mixtures which have proven particularly useful are those of CaO and NaOH, and of MgO and NaOH, being made of BaO as a further suitable metal oxide.

Particularly suitable glycol ethers are those of the formula $R^1—O—(CH_2CH_2—O)_n—R^2$, where $R^1$ and $R^2$ are, independently of one another, an alkyl or aryl group and n=1-12.

For metallation with sodium, glycol diethers having $R^1=R^2=$ethyl, n=2; $R^1=R^2=$methyl, n=2; or $R^1=R^2=$methyl, n=3 are particularly suitable.

If metallation is being carried out with alkyllithiums, additional glycol diethers which are particularly suitable are those having $R^1=R^2=$methyl, n=1; $R^1=R^2=$ethyl, n=1.

Then monomeric cyclopentadiene is metered in, followed by the radical R to be substituted which is provided in the form RX.

After the reaction has ended, the sparingly-soluble salts which are produced are separated off and, if necessary, volatile excess starting materials are removed.

The organic phase can subsequently be used further without isolation of the reaction product, the metallation of the substituted cyclopentadiene being effected according to methods known in the literature.

Of particular suitability are for example sodium, sodium hydride and alkyllithiums. The addition of the transition metal halide follows directly after.

After separating off the inorganic salts produced, the desired metallocene is isolated and optionally purified further by means of recrystallization.

The raw material CaO/NaOH is available at a favorable price and, in comparison with other metallating agents such as sodium or alkyllithiums, can be handled safely.

In the reaction of cyclopentadiene with RX, no multiple substitution is observed, as is the case, for example, when using elemental sodium or alkyllithiums as metallating agents. The substitution product formed is exclusively the monosubstituted cyclopentadiene derivative.

This is all the more surprising as it is claimed that solvents having much higher dielectric constants than THF (e.g. acetonitrile or dimethylformamide) are required when using CaO/NaOH as metallating agent in reactions such as equation I (dielectric constants of: acetonitrile: 35.92; dimethylformamide: 36.71; compared with glycol diethers: 5.7–7.8) (reference: Vestsi Akad. Navuk. BSSR, Ser. Khim Navuk., 1988(1), pp. 96–97; CA:(109)148913 q).

The use of glycol diethers makes possible both the removal of any traces of volatile starting materials still present after the reaction according to equation I and prior to the reaction according to equation II, which can further increase the purity of the final product, and also the direct further metallation and reaction with a corresponding transition metal compound to give the desired metallocene.

EXAMPLES

EXAMPLE 1

Preparation of bis(n-butylcyclopentadienyl)-$ZrCl_2$

At 10° C., 14.3 g (216 mmol) of monomeric cyclopentadiene was added dropwise to a mixture of 150 ml of diethylene glycol diethyl ether and 27.5 g of powdered CaO/NaOH (286 mmol of each). Immediately afterwards, 19.6 g (143 mmol) of n-butyl bromide was metered in. The mixture was stirred for a further 4 hours at room temperature.

The excess cyclopentadiene was drawn off by means of a light vacuum and the inorganic salts were separated off by filtration. According to gas chromatography (GC), the yields of n-butylcyclopentadiene were 95%.

The n-butylcyclopentadiene was metallated by addition of 2.96 g of sodium (129 mmol) and stirring at 170° C.

After hydrogen evolution ended and the sodium had completely reacted, the mixture was cooled to −10° C. and 15 g of $ZrCl_4$ (64.4 mmol) was added.

After 30 minutes of stirring at room temperature, the solution was freed of precipitated NaCl. Distilling off the solvent gave 23 g of crude product (57 mmol); 88% yield, based on $ZrCl_4$).

After recrystallization from heptane, 19.9 g (76%, based on $ZrCl_4$) of pure product was obtained.

$^1$H-NMR spectrum ($CDCl_3$):6.3-6.13 (m, 8H, $—C_5H_4$); 2.6 (t, 4H, $—CH_2—$); 1.5 (quintet, 4H, $—CH_2—$); 1.35 (sextet, 4H, $—CH_2—$); 0.9 (t, 6H, $CH_3$).

Amount of unsubstituted cyclopentadiene groups in the product ($^1$H-NMR:integral in the range 6.3–7 ppm):1.4%.

Elemental analysis: Zr: found:22.50 (calc.: 22.55); Cl: found: 17.55 (calc.: 17.53).

COMPARATIVE EXAMPLE

At room temperature, 14.3 g (143 mmol) of monomeric cyclopentadiene was added dropwise to a suspension of 5.3 g of NaH (170 mmol) and the mixture was stirred until gas evolution was no longer observed.

Excess NaH was filtered off and the cyclopentadienylsodium solution was admixed dropwise at 10° C. with 19.6 g (143 mmol) of n-butyl bromide.

After 4 hours of further reaction at room temperature, a sample was analyzed by gas chromatography.

In addition to 78% of the desired n-butylcyclopentadiene, the reaction solution also contained 4.5% of cyclopentadiene, 16% of dibutylcyclopentadiene and 1% of tributylcyclopentadiene. The reaction solution was freed of excess cyclopentadiene by application of vacuum.

The remaining cyclopentadiene derivatives were metallated with 129 mmol of sodium at 170°-180° C. After hydrogen evolution ended, the mixture was cooled to −10° C. and 15 g of $ZrCl_4$ was added.

After 30 minutes of stirring, the solution was freed of the precipitated inorganic salts and the solvent was removed by distillation. After recrystallization from 200 ml of n-heptane, 13.8 g of product were obtained in 53% yield (based on $ZrCl_4$).

Analysis by $^1$H-NMR spectroscopy revealed that the product contained only 80% of n-butylcyclopentadienyl groups. The remaining 20% were cyclopentadienyl or multiply butylated cyclopentadiene groups (according to $^1$H-NMR; integral from 6.3-7.0 ppm).

EXAMPLE 1*a*

The procedure was analogous to Example 1. However, BaO was used in place of CaO. GC analysis gave a yield of n-butylcyclopentadiene of 93%. No overalkylation at all was observed, unlike the above comparative example.

After further reaction and workup, bis(n-butylcyclopentadienyl)$ZrCl_2$ was obtained in 78% yield.

EXAMPLE 2

Preparation of bis(n-butylcyclopentadienyl)$ZrCl_2$ n-Butylcyclopentadiene was prepared analogously to Example 1 and freed or inorganic salts and excess cyclopentadiene. The solution so obtained was cooled to 0° C. and subsequently admixed dropwise with 9.7 g of n-butyllithium (90% strength in hexane; 136 mmol). The mixture was allowed to react for a further 30 minutes while stirring. 15.8 g of $ZrCl_4$ (68 mmol) was added at 0°-10° C. and the mixture was stirred for 2 hours at room temperature.

The diethylene glycol diethyl ether was removed in vacuo, the residue was taken up in 90 ml of toluene and freed of precipitated LiCl.

The toluene was distilled off and replaced by 300 ml of heptane. After refluxing for 10 minutes, the mixture was cooled to room temperature and further material was crystallized out overnight in a deep freezer at −20° C. Isolation of the product by filtration and drying in vacuo gave 20.6 g of pure product (75% yield, based on $ZrCl_4$).

$^1$H-NMR: identical to that in Example 1.

Elemental analysis: Zr: found: 22.51% (calc.: 22.55%); Cl: found: 17.50% (calc.: 17.55).

Amount of unsubstituted cyclopentadienyl groups in the product: (according to $^1$H-NMR: integral 6.3-7.0 ppm): <0.1%).

The metallation by means of n-butyllithium is advantageous insofar as, unlike Example 1, the monomeric cyclopentadiene used can also contain high proportions of dicyclopentadiene without the proportion of unsubstituted cyclopentadiene groups in the product rising.

EXAMPLE 3

The procedure was analogous to Example 2, except that the monomeric cyclopentadiene also contained 15% of dicyclopentadiene. After carrying out the synthesis, 21.7 g (79%) of pure product was obtained (unsubstituted cyclopentadiene groups in the product according to $^1$H-NMR: <1%).

EXAMPLE 4

The procedure was analogous to Example 2. In place of butyl bromide, butyl iodide was used. 19.7 g (71%) of pure product was isolated.

EXAMPLE 5

The procedure was analogous to Example 2, but using iso-butyl bromide in place of n-butyl bromide. After workup, 20.5 g of product (74.5%) was isolated.

$^1$H-NMR spectrum ($CDCl_3$): 6.28-6.18 (m, 8H, $-C_5H_4$); 2.46 (d, 4H, $CH_2$); 1.74 (nonet, 2H, CH); 0.86 (d, 6H, $CH_3$).

Unsubstituted cyclopentadiene groups in the product (according to $^1$H-NMR: integral from 6.28-7 ppm): 1.9%.

Zr: found: 22.50 (calc.: 22.55); Cl: found: 17.25 (calc.: 17.55).

EXAMPLE 6

The procedure was analogous to Example 2, using cyclopentyl bromide as alkyl halide. 18.4 g of product was isolated in 63% yield (based on $ZrCl_4$).

$^1$H-NMR: 6.28-6.18 (m, 8H, $-C_5H_4$); 3.15 (quintet, 2H, CH); 2.1-1.9 (m, 4H, $-CH_2-$), 1.74-1.4 (m, 12H, $-CH_2-$).

Zr: found: 21.40 (calc.: 21.29); Cl: found: 16.50 (calc.: 16.55).

EXAMPLE 7

The procedure was analogous to Example 2. Diethylene glycol dimethyl ether was used in place of diethylene glycol diethyl ether. 21 g of pure product was obtained.

EXAMPLE 8

The procedure was analogous to Example 2. Triethylene glycol dimethyl ether was used in place of diethylene glycol diethyl ether. 20.1 g of pure product was isolated.

EXAMPLE 9

The procedure was analogous to Example 2. Benzyl chloride was used in place of n-butyl bromide. 19.8 g of pure product was isolated.

$^1$H-NMR ($CDCl_3$): 7.4-7.0 (m, 10H, $C_6H_5$); 6.3-6.1 (m, 8H, $C_5H_4$); 4.0 (s, 4H, $-CH_2-$).

It is advantageous to employ the metal oxide/hydroxide used for metallation in an excess of 0-100%, preferably 10-50%, the cyclopentadiene in an excess of 0-100% preferably 10-30%, with the cyclopentadiene being able to contain any desired amount of dicyclopentadiene (preferably 0-30%).

The reaction is carried out at temperatures from −20° to 200° C., preferably from −10° to 170° C., when metallating with sodium, from −10° to 30° C. when metallating with alkyllithium.

EXAMPLE 10

The procedure was analogous to Example 2. However, MgO was used in place of CaO. After reaction of the cyclopentadiene with n-butylbromide, up to 95% of n-butylCp was obtained (GC monitoring).

Further reaction and isolation of the final product gave 75% of theoretical bis(n-butylcyclopentadienyl)$ZrCl_2$.

EXAMPLE 11

Preparation of bis(n-butylcyclopentadienyl)$TiCl_2$

The procedure was analogous to Example 2. In place of $ZrCl_4$, 12.2 g of $TiCl_4$ (64.4 mmol) was added.

17 g of product (47 mmol; 73% of theoretical based on $TiCl_4$) was isolated in the form of a pale red solid.

$^1$H-NMR ($CDCl_3$) 6.4–6.3 (m, 8H, —$C_5H_4$); 2.68 (t, 4H, —$CH_2$—) 1.53 (quintet; 4H, —$CH_2$—); 1.33 (sextet; 4H, —$CH_2$—); 0.9 (t, 6H, $CH_3$).

Ti: found: 13.4% (calc.: 13.25)); Cl: found: 19.6% (calc.: 19.6).

EXAMPLE 12

Preparation of bis(n-butylcyclopentadienyl)$HfCl_2$

The procedure was analogous to Example 2. In place of $ZrCl_4$, 20.6 g of $HfCl_4$ was used. 25.1 g of product was isolated as a white solid (51 mmol; 79% of theoretical based on $HfCl_4$).

$^1$H-NMR ($CDCl_3$) 6.22–2.09 (m, 8H-$C_5H_4$); 2.66 (t, 4H, —$CH_2$—) 1.53 (quintet, 4H, —$CH_2$—); 1.34 (sextet; 4H, —$CH_2$—); 0.92 (t, 6H, —$CH_3$).

Hf: found: 37.7% (calc.: 36.3%); Cl: found: 14.5% (calc.: 14.4%).

EXAMPLE 13

Preparation of bis(i-propylcyclopentadienyl)$ZrCl_2$

At 10° C., 42.6 g (0.64 mol) of monomeric cyclopentadiene was added dropwise to a mixture of powdered CaO (48.1 g) and NaOH (34.32 g) in 450 ml of ethylene glycol dimethyl ether. Immediately afterwards, 52.8 g (0.43 mol) of 2-bromopropane was added over a period of 75 minutes.

The mixture was stirred for a further 4 hours at room temperature and subsequently the conversion was monitored by means of GC analysis. 93% of i-propylcyclopentadiene was formed. Inorganic salts were separated off by filtration.

To remove excess volatile starting materials, 200 ml of diethyl ether was added and drawn off again by application of vacuum.

The solution so obtained was admixed at 0° C. with ml of n-BuLi (2.5 molar in hexane; 0.3 mol).

The mixture was allowed to react further for 1 hour while stirring at room temperature. 34.95 g of $ZrCl_4$ (0.15 mol) was introduced between 0°–10° C. and reacted for 2 hours at room temperature while stirring.

All volatile components were distilled off and the residue was taken up in 300 mol of toluene and freed of the inorganic salts by filtration.

The toluene was distilled off and replaced by 500 ml of heptane. After refluxing for 30 minutes, the mixture was crystallized at −20° C.

44 g (78%) of bis(i-propylcyclopentadienyl)$ZrCl_2$ was isolated.

$^1$H-NMR: ($CDCl_3$) 6.28–8.18 (m, 8H, —$C_5H_4$); 3.09 (septet, 2H, —CH—); 1.18 (d, 12H, —$CH_3$).

Zr: found: 24.0 (calc.: 24.2); Cl: found: 18.1 (calc.: 18.8).

EXAMPLE 14

Preparation of bis(octadecylcyclopentadienyl)$ZrCl_2$

The procedure was analogous to Example 2. In place of n-butyl bromide, octadecyl bromide was used. 39.3 g (72.5% yield of theoretical; calculated on the basis of $ZrCl_4$) of product was isolated.

$^1$H-NMR: ($CDCl_3$) 6.28–6.19 (m, 8H, —$C_5H_4$); 2.60 (t, 4H, —$CH_2$—); 1.53 (m, 4H, —$CH_2$—); 1.25 (m, 30H, —$CH_2$); 0.87 (t, 6H, —$CH_3$).

Zr: found: 11.4 (calc.: 11.4); Cl: found: 8.4 (calc.: 8.9).

What is claimed is:

1. A process for the preparation of transition metal complexes having monosubstituted cyclopentadienyl ligands of the general formula:

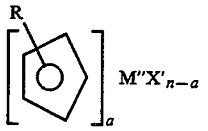

where

R is a $C_1$–$C_{30}$-alkyl group, $C_2$–$C_{30}$-alkenyl group, $C_7$–$C_{30}$-alkylaryl group, $C_8$–$C_{30}$-alkenylaryl group, $C_3$–$C_{12}$-alkoxyalkyl group, $C_1$–$C_{30}$-fluoroalkyl group or $C_1$–$C_6$-alkyl-tri($C_1$–$C_{10}$-alkyl)-silyl;

M″ is a transition metal selected from the group consisting of Ti, Zr, Hf, Fe, V, Cr, Sc, and mixture thereof;

X′ is selected from the group consisting of Cl, Br, Y, I, and mixtures thereof;

n is the oxidation number of the transition metal;

a is at least 1 and a is ≦n, comprising reacting monomeric cyclopentadiene with an organic halide in the presence of a metallating agent comprising a mixture of an alkali metal oxide or hydroxide and an alkaline earth metal oxide or hydroxide in glycol diether as solvent, thereby forming an intermediate monosubstituted cyclopentadiene, and reacting said intermediate in situ with a transition metal halide to form the final product.

2. A process according to claim 1, characterized in that the substituent R is a $C_3$–$C_{18}$-alkyl group, $C_2$–$C_{18}$-alkenyl group, $C_3$–$C_6$-alkoxyalkyl group or $C_1$–$C_3$-alkyl-tri-($C_1$–$C_6$-alkyl)-silyl group.

3. A process according to claim 2, characterized in that R is a $C_3$–$C_8$-alkyl group or $C_2$–$C_6$-alkenyl group.

4. A process according to one of claims 1 to 3 characterized in that the transition metal is titanium, zirconium or hafnium.

5. Bis(octadecylcyclopentadienyl)$ZrCl_2$).

* * * * *

UNITED STATES PATENT AND TRADEMARK OFFICE

CERTIFICATE OF CORRECTION

PATENT NO. : 5,336,795
DATED : August 9, 1994
INVENTOR(S) : Richard Lisowsky

It is certified that error appears in the above-indentified patent and that said Letters Patent is hereby corrected as shown below:

Column 3, line 14: before "is a" insert --R--

Column 3, line 38: before "being" insert --mention--

Signed and Sealed this

Tenth Day of January, 1995

Attest:

BRUCE LEHMAN

Attesting Officer

*Commissioner of Patents and Trademarks*

--